United States Patent [19]

Linstid, III

[11] Patent Number: 5,191,133

[45] Date of Patent: Mar. 2, 1993

[54] PROCESS FOR PREPARATION OF 2-VINYLNAPHTHALENE

[75] Inventor: Henry C. Linstid, III, Clinton, N.J.

[73] Assignee: Hoescht Celanese Corporation, Somerville, N.J.

[21] Appl. No.: 704,574

[22] Filed: May 22, 1991

[51] Int. Cl.$^5$ ................................................ C07C 1/24
[52] U.S. Cl. .................................... 585/437; 568/808; 568/814; 568/319; 568/323
[58] Field of Search ............... 568/319, 323, 808, 814; 585/437

[56] References Cited

U.S. PATENT DOCUMENTS

| | | | |
|---|---|---|---|
| 2,468,759 | 5/1949 | Johnson | 260/669 |
| 4,082,807 | 4/1978 | Eiglmeier | 568/316 |
| 4,593,125 | 6/1986 | Davenport et al. | 568/319 |
| 4,990,681 | 2/1991 | Curtis et al. | 568/319 |
| 4,996,374 | 2/1991 | Lin et al. | 568/814 |

OTHER PUBLICATIONS

Petrov et al., Chem. Abst., vol. 100, #192,316k (1984).
Xia et al., Chem. Abst., vol. 96, #84,841t (1982).
Chem. Abst., vol. 96, #34,791f (1982).

*Primary Examiner*—James H. Reamer
*Attorney, Agent, or Firm*—S. D. Frenkel; D. R. Cassady

[57] ABSTRACT

The selective formation of 2-acetonaphthalene is achieved by acetylating naphthalene in the presence of liquid hydrogen fluoride. The 2-acetonaphthalene can be separated from the formed 1-acetonaphthalene isomer by successive hydrogenation of the isomer mixture and dehydration. The hydrogenation is selective to the 2-isomer while the 1-acetonaphthalene remains unreacted. Upon completion, 2-vinylnaphthalene can be distilled off from the unreacted 1-acetonaphthalene.

15 Claims, No Drawings

PROCESS FOR PREPARATION OF 2-VINYLNAPHTHALENE

BACKGROUND OF THE INVENTION

The present invention is directed to the preparation of 2-vinylnaphthalenes. The 2-vinylnaphthalenes have use as monomers in the production of vinylnaphthalene polymeric materials.

One route proposed for the preparation of 2-vinylnaphthalene begins with the hydrogenation of 2-acetonaphthalene and subsequent dehydration of the formed 2-methylnaphthyl carbinol. The reaction mechanism which has been proposed is as follows:

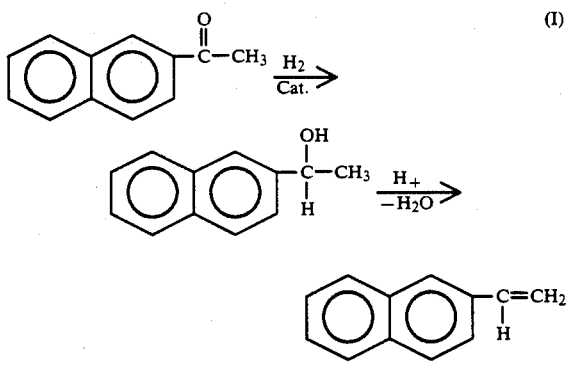

Unfortunately, 2-acetonaphthalene is relatively expensive in the pure form due to the poor selectivity which is achieved in acetylating naphthalene to the 2-isomer and in view of the yield loss which is incurred in separating the 2-acetonaphthalene from the 1-isomer.

It is possible to obtain vinylnaphthalene by dehydrogenating ethyl naphthalene. As simple as this process appears, however, it is complicated by the difficulty of recovering the vinylnaphthalene from the reaction mixture. The vinylnaphthalene so readily polymerizes that it is difficult to separate vinylnaphthalene from the unchanged ethyl naphthalene by distillation. A proposed route to forming vinylnaphthalene from ethyl naphthalene is disclosed in U.S. Pat. No. 2,468,759. As disclosed therein, a mixture of 1- and 2-ethyl naphthalene is oxidized to a mixture of methylnaphthyl carbinol and methylnaphthyl ketone. The methylnaphthyl ketone is hydrogenated to methylnaphthyl carbinol and the methylnaphthyl carbinol dehydrated to vinyl naphthalene. The process involves at least three steps in addition to obtaining the starting ethyl naphthalene.

It would appear, however, that a key step in producing pure 2-vinylnaphthalene by the process as disclosed in the patent would become the separation from any coproduced 1-vinylnaphthalene. The patent is silent as to the isomers produced.

Accordingly, it is an object of the present invention to provide an improved process for the production of 2-vinylnaphthalenes which is more economical than previously proposed.

SUMMARY OF THE INVENTION

In accordance with the present invention, it has been discovered that a 2-acylnaphthalene (e.g. 2-acetonaphthone) in the presence of a 1-acylnaphthalene (e.g. 1-acetonaphthone) can be selectively hydrogenated. This discovery provides for ready separation of 2-substituted naphthalene products from 1-substituted naphthalene products, inasmuch as the physical properties of the hydrogenated 2-acylnaphthalene (e.g. 1-(naphth-2-yl)ethanol) are sufficiently different from the 1-acylnaphthalene. Accordingly, it is possible to separate these materials using techniques such as distillation prior to dehydration of the alcohol to the respective 2-vinylnaphthalene.

Alternatively, the dehydration of the hydrogenated 2-acylnaphthalene may take place in the presence of the unreacted 1-acylnaphthalene. In this case dehydration is performed under conditions favoring the distillation of the 2-vinylnaphthalene. Under such conditions, the vinyl compound is rapidly separated, side reactions (e.g. polymerization, Prins reaction) are minimized, and yield is maximized.

DETAILED DESCRIPTION OF THE INVENTION

The present invention is generally concerned with a process for producing 2-acylnaphthalenes and further to producing therefrom 2-vinylnaphthalene and 1-vinylnaphthalene monomers which have use in producing vinyl polymers.

In accordance with the present invention, acylation of naphthalene is produced by treating naphthalene in anhydrous liquid hydrofluoric acid with a carboxylic acid, halide or anhydride of the formula:

wherein R is an alkyl group containing, for example, from 1 to 12 carbon atoms, or an aryl group, or substituted alkyl or aryl groups. X is a halide selected from F, Cl, Br and I or X stands for OR', wherein R' is hydrogen or equivalent to a

group to provide a carboxylic acid or an acid anhydride as the acylating agent. It has been found that acylation in the presence of HF is selective to the formation of the 2-acyl isomer which has the general structural formula:

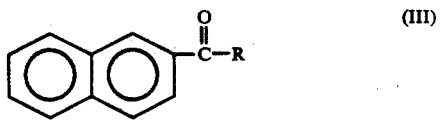

wherein R is as defined above. Acylation proceeds as shown in equation (IV) below.

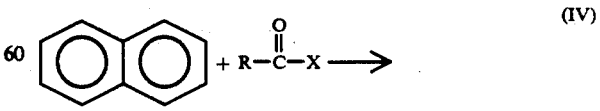

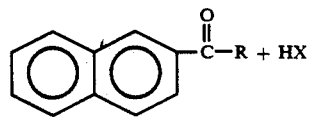

The present invention is particularly concerned with forming 2-acetonaphthalene (R is methyl) and eventually 2-vinylnaphthalene monomer which can be used in the formation of vinyl polymers. Thus, it has been found that acetylation of naphthalene with acetic acid, acetyl halide or acetic anhydride results in the favorable formation of 2-acetonaphthalene by a ratio of about 3:1 relative to the 1-aceto isomer. The present inventors have discovered further that the separation of the isomers can be readily achieved by hydrogenation of the acetylation product inasmuch as it has been found that 1-acetonaphthalene hydrogenates at a significantly slower rate than 2-acetonaphthalene in the presence of a hydrogenation catalyst. Accordingly, by hydrogenating the acetylation product, only the 2-acetonaphthalene is converted to the corresponding alcohol. Subsequent dehydration yields 2-vinylnaphthalene. The alcohol or the 2-vinylnaphthalene can be distilled away from the 1-acetonaphthalene which remains unreacted during hydrogenation and dehydration. The 1-acetonaphthalene obtained from the residue can then be converted to 1-vinylnaphthalene, 1-naphthol or other 1-substituted naphthalene derivatives.

The reaction scheme for the process of this invention can be shown as follows:

residue using alternative conditions or methods, and analogous dehydration.

The acylation reaction (IV) according to this invention is carried out in anhydrous liquid hydrofluoric acid. The hydrofluoric acid may be of technical grade but should not contain more than about 5 wt. % water. Although a solvent is not necessary for the reaction, a known Friedel-Crafts reaction solvent can be used.

The acylation reaction according to the invention may be carried out at temperatures between about room temperature to 120° C., preferably between about 40° and 70° C. The reaction time is generally between about 30 minutes and 8 hours. The reaction can be carried out at atmospheric pressure and, if necessary, also at elevated pressure, up to about 150 psig.

The mole ratio of HF to naphthalene should be between about 1 and 100. It is preferred to provide a molar excess of the carboxylic acid, halide or anhydride acylating agent relative to the amount of naphthalene present. Thus, for every mole of naphthalene there should be present about 1 to 2 moles of acylating agent.

The naphthalene and acylating agent can be mixed together in the reactor prior to addition of HF or the acylating agent may be added subsequent to the addition of HF to the naphthalene. Upon addition of the HF,

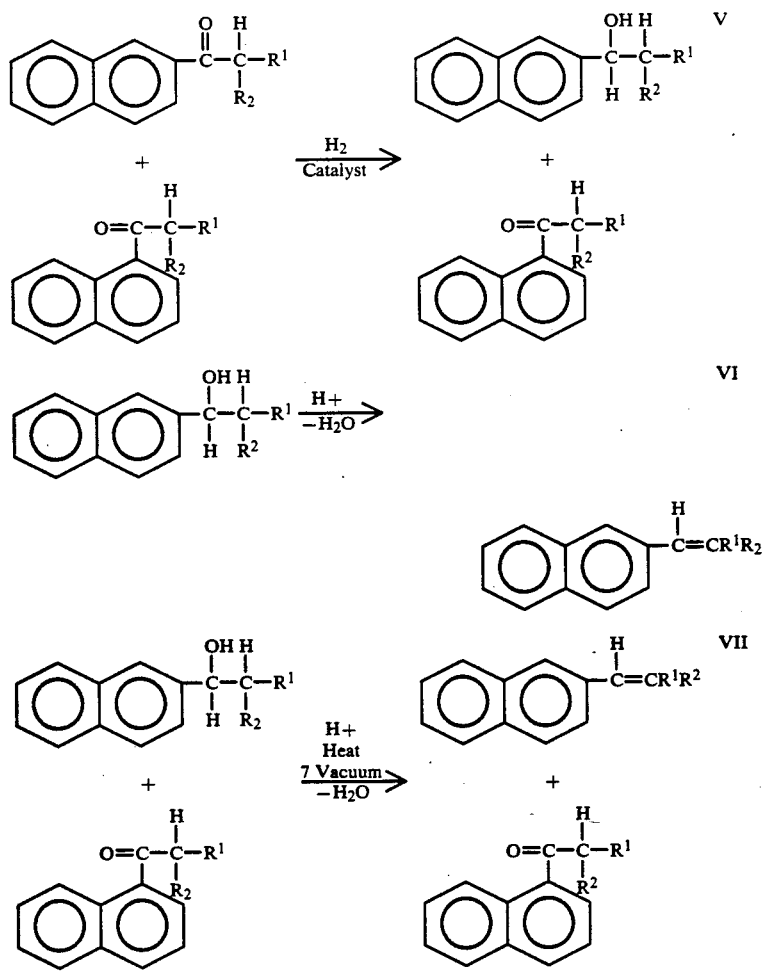

$R^1$ and $R^2$ can be H or alkyl comprising from 1 to 12 carbon atoms.

The 1-acylnaphthalene can be converted to a pure 1-vinylnaphthalene by hydrogenation of the distillation the reaction pressure increases. At this time, the reactants can be brought to reaction temperature which is maintained to completion of the reaction. The acylated product can be separated by distillative separation of the HF from the reaction products. The HF can thus be recovered and recycled to the process.

In the process of this invention where acetylation of naphthalene is used to produce acetonaphthalenes, the 2-acetonaphthalene can be separated from the 1-isomer by converting the 2-acetonaphthalene to 2-vinylnaphthalene by the process scheme as above described and depicted in equations V, VI and VII. Hydrogenation of the product of acetylation (V) yields 2-methylnaphthyl carbinol and unreacted 1-acetonaphthalene. Hydrogenation can take place at a hydrogen pressure of from between about 50 to 500 psig, and at a temperature from between about 40° to 175° C. Less severe conditions within the listed ranges of pressure and temperature are preferred. Thus, hydrogen pressures less than 250 psig and temperatures less than 100° C. are especially preferred. A hydrogenation catalyst is preferably present in the reaction medium. Any hydrogenation catalyst can be utilized. For example, the group VIII metals including nickel, palladium, platinum, ruthenium, etc can be used. Copper chromite is also useful in hydrogenating 2-acetonaphthalene. Palladium is preferred along with the less severe conditions as this combination provides selectivity to hydrogenating the 2-isomer while leaving the 1-isomer unreacted. The catalyst can be used unsupported or it can be supported on a suitable carrier such as silica, alumina, silica-alumina, and like carriers. Carbon is also a suitable carrier for the hydrogenation catalyst.

The crude hydrogenated product may therefore be treated to recover the desired methylnaphthyl carbinol in a relatively pure form. This may be effected by distilling the crude hydrogenation product at a pressure sufficiently below atmospheric to give a temperature below that which substantial dehydration of the methylnaphthyl carbinol takes place. Alternatively, it has been found that 2-methylnaphthyl carbinol which is produced can be dehydrated in the presence of 1-acetonaphthalene to yield 2-vinylnaphthalene. The 1-acetonaphthalene remains unreacted.

In accordance with this invention, the 2-methylnaphthyl carbinol produced from the hydrogenation operation can be converted to vinyl naphthalene by dehydration of the 2-methylnaphthyl carbinol (VI) or an unseparated mixture of 2-methylnaphthyl carbinol and 1-acetonaphthalene (VII). Either of reactions VI or VII may take place in the gas phase in which the reactants are contacted with an acidic dehydration catalyst which suitably is a surface catalyst such as activated alumina. Under suitable conditions of temperature and pressure, dehydration of the 2-methylnaphthyl carbinol is effected. At a temperature of at least 300° C., and in the presence of a suitable dehydration catalyst, 2-methylnaphthyl carbinol may be substantially completely dehydrated. Unless care is utilized, however, the vinylnaphthalene formed in the dehydration is substantially polymerized.

In order to avoid polymerization of vinyl naphthalene in the dehydration, it is necessary to effect a suitable balance between the temperature of the dehydration reaction and the time of exposure. If the temperature is too high or if the time is too low, undesirable polymerization of vinylnaphthalene takes place. It has been found that temperatures between about 300° and 350° C. with a surface catalyst, such as activated alumina, the space-velocity may easily be so regulated as to obtain high conversion of 2-methylnaphthyl carbinol to vinylnaphthalene with substantially no polymerization. The dehydration is most suitably effected at atmospheric pressure although higher or lower pressures, while not economical, nevertheless may be used. It is desirable to reduce the partial pressure of the 2-methylnaphthyl carbinol vapors over the surface catalyst by diluting them with a suitable inert diluent gas such as carbon dioxide.

A product may be thus obtained which is sufficiently pure for technical purposes. Where a more highly refined product is desired however or where the dehydration through inactivation of catalyst leaves a substantial proportion of the methylnaphthyl carbinol unchanged, the product may be purified by distillation at a pressure sufficiently below atmospheric to give a temperature below that at which substantial polymerization of vinylnaphthalene takes place. Further, since the boiling point of 1-acetonaphthalene is 30° C. higher than 2-vinylnaphthalene, separation may be easily effected. By effecting distillation at a pressure suitably low, e.g., 20 mm Hg, the 2-vinylnaphthalene may be distilled free of the 1-acetonaphthalene without objectionable polymerization.

Inasmuch as it is relatively easy to separate the 2-vinylnapthylene from the unreacted 1-acetonaphthalene, it is preferred to perform the dehydration reaction (VII) in the liquid phase in the presence of a dehydration catalyst. Typical liquid phase dehydration catalysts are acid catalysts such as various mineral acids such as hydrochloric acid, phosphoric acid, sulfuric acid, etc. A preferred acid catalyst is potassium hydrogen sulfate. During the liquid phase dehydration reaction, the 2-vinylnaphthalene is formed and temperature and pressure (preferably a vacuum) are controlled so as to allow the 2-vinylnaphthalene products to be distilled from the 1-acetonaphthalene. A liquid phase reaction can also be used to dehydrate the pure 2-methylnaphthyl carbinol (VI).

The process according to this invention including reaction and recover of the product is illustrated in greater detail in the following examples. Unless otherwise indicated, all percentage amounts are weight percent.

EXAMPLE 1

12.8 g (0.1 mole) of naphthalene and 11.2 g (0.22 mole) of acetic anhydride were placed in a 300 mL Hastelloy C autoclave and the reactor sealed. The reactor was checked for leaks with 80 psig $N_2$, the nitrogen evacuated from the reactor, and the reactor cooled to $-30°$ C. with a dry ice/isopropanol bath. The reactor was purged twice with $N_2$. 100 g of HF was transferred to the reactor and the reactor was heated to 50° C. and maintained for one hour. The reactor was cooled to $-30°$ C. with a dry ice/isopropanol bath. The contents of the reactor were removed by pressuring the reactor with $N_2$ and draining the solution through a feed line. After the solution had been drained onto ice, it was neutralized with a 50% KOH solution to pH 6.5. The organic phase was extracted with ethylacetate, dried over $MgSO_4$, filtered and concentrated. 13.2 g was recovered.

EXAMPLE 2

12.8 g naphthalene and 51.0 g acetic anhydride were placed into a 300 mL Hastelloy C autoclave and the reactor sealed. The reactor was pressure checked with 80 psig $N_2$ as in Example 1. The reactor was cooled to −30° C. with a dry ice/isopropanol bath. 100 g HF was added to the reactor and the reactor heated to 40° C. and maintained for 5.5 hours. The reactor was cooled to −30° C. with a dry ice/isopropanol bath. The contents of the reactor were removed by pressuring the reactor with and draining the solution through a feed line. After the solution had been drained onto ice, it was neutralized to a pH of 6.5 with KOH, 50% solution. The product was extracted with ethyl acetate, dried over $MgSO_4$, filtered and concentrated to yield 12.5 g net product.

EXAMPLE 3

The same procedure of Example 2 was followed to acetylate naphthalene with acetic anhydride except 5.1 g of acetic anhydride was used. 11.92 g of product was recovered.

EXAMPLE 4

A solution of 12.8 g. (0.1 moles) of naphthalene and 20.4 g. (0.2 moles) of acetic anhydride was cooled to −30° C. in a Hastalloy C autoclave. The vessel was purged by alternately evacuating and filling with nitrogen. Hydrogen fluoride, 100 g. (5.0 moles) was added and the autoclave sealed.

The autoclave was rapidly heated to 80° C. and maintained at that temperature for 60 minutes. The autoclave was then rapidly cooled to <0° C. and the contents poured onto ice. Ethyl acetate was added to dissolve the organic products and an aqueous solution of 45% potassium hydroxide was added to neutralize the solution. The ethyl acetate layer was separated and the aqueous layer repeatedly extracted with fresh ethyl acetate to recover additional products. The organic layers were combined, washed with a saturated aqueous sodium chloride solution, dried over anhydrous magnesium sulfate, and the solvent removed in vacuo. Conversion 90%, selectivity to 1-acetonaphthone 17%, selectivity to 2-acetonaphthone 48%, accountability 68%.

EXAMPLE 5

This example describes the hydrogenation of an acetonaphthone mixture in which the 2-isomer reacts and the 1-isomer does not.

A one-to-one mixture of 1- and 2-acetonaphthone (85 g., 0.5 mole) was dissolved in 300 mL of tetrahydrofuran (THF). This solution was placed in a 500 cc reactor along with 10 g of palladium supported on carbon. The reactor was sealed, deaerated with nitrogen, and pressured to 100 psig with hydrogen. The reaction was heated to 50° C. and continued until approximately 0.25 moles of hydrogen was taken up. The catalyst was filtered away from the THF solution and the solvent removed in vacuo. The 1-acetonaphthone was essentially unreacted while 70% of the 2-isomer was converted to the alcohol.

EXAMPLE 6

72.43 g of a mixture of 1-acylnaphthalene and 2-methyl-naphth−2-ylcarbinol (1:1 molar ratio) are added to 0.74 g potassium hydrogen sulfate and 0.08 g of t-butylcatechol in a 250 ml round bottom flask which is placed in a hot oil bath. The hot oil bath is maintained at a temperature of 160° C. and the mixture heated for ½ hour under a vacuum of 1.3 mm Hg. For the next hour, distillation of most of the formed water and 2-vinyl naphthalene begins and the distillate is collected. Distillation continues for another hour.

The product is dissolved in hexane and the aqueous phase separated. Rigorously dry material can be prepared by treating this solution with calcium hydride followed by distillation. The conversion of carbinol is 99% with a 57% yield of 2-VN. Primary yield loss is due to oligomerization of 2-VN which remains at the bottom of the flask.

What is claimed is:

1. A process for synthesizing 2-vinylnaphthalene comprising selectively hydrogenating a first mixture of 2-acetonaphthalene and 1-acetonaphthalene to form a second mixture including 2-methylnaphthyl carbinol and unreacted 1-acetonaphthalene followed by dehydrating said second mixture to yield 2-vinyl naphthalene, wherein the dehydration product consists substantially exclusively of 2-vinyl naphthalene.

2. The process according to claim 1, wherein said first mixture of 2-acetonaphthalene and 1-acetonaphthalene is produced by acylating naphthalene with an acylating agent comprising a carboxylic acid, halide or anhydride in the presence of liquid HF such that said mixture contains more than 50% by weight 2-acetonaphthalene based on the combined weight of 1-acetonaphthalene and 2-acetonaphthalene.

3. The process of claim 1 wherein said acylating agent is acetic acid, acetyl halide or acetic anhydride to selectively produce 2-acetonaphthalene.

4. The process of claim 3 wherein said acylating agent is acetic anhydride.

5. The process of claim 1 wherein the acylation temperature ranges from about room temperature to about 120° C.

6. The process of claim 5 wherein said reaction temperature ranges from about 40° to about 70° C.

7. The process of claim 1 wherein the acylation pressure ranges from about atmospheric pressure to about 150 psig.

8. A process for synthesizing 2-vinyl naphthalene comprising reacting naphthalene with an acetylating agent comprising acetic acid, acetyl halide or acetic anhydride in the presence of HF to acetylate the naphthalene ring to yield a mixture of 2-acetonaphthalene and 1-acetonaphthalene, hydrogenating the mixture of isomers to form a mixture of 2-methylnaphthyl carbinol and unreacted 1-acetonaphthalene, dehydrating the product of said hydrogenation to yield 2-vinylnaphthalene.

9. The process of claim 1 wherein said hydrogenation takes place in the presence of a hydrogenation catalyst.

10. The process of claim 1 wherein said dehydration takes place in the presence of a dehydration catalyst.

11. The process of claim 1 wherein said 1-acetonaphthalene is separated from said 2-vinyl naphthalene subsequent to said dehydration reaction.

12. The process of claim 1 wherein said 1-acetonaphthalene is separated from said carbinol prior to said dehydration.

13. The process of claim 9 wherein said hydrogenation catalyst is palladium.

14. The process of claim 13 wherein said hydrogenation takes place at a temperature of from about 40° C. to 100° C.

15. The process of claim 13 wherein said dehydration takes place in the liquid phase in the presence of an acid catalyst.

* * * * *